US011763932B2

(12) United States Patent
Levanony et al.

(10) Patent No.: US 11,763,932 B2
(45) Date of Patent: Sep. 19, 2023

(54) CLASSIFYING IMAGES USING DEEP NEURAL NETWORK WITH INTEGRATED ACQUISITION INFORMATION

(71) Applicant: International Business Machines Corporation, Armonk, NY (US)

(72) Inventors: Dana Levanony, Tel-Aviv (IL); Efrat Hexter, Beit Shemesh (IL)

(73) Assignee: International Business Machines Corporation, Armonk, NY (US)

( * ) Notice: Subject to any disclaimer, the term of this patent is extended or adjusted under 35 U.S.C. 154(b) by 600 days.

(21) Appl. No.: 16/683,305

(22) Filed: Nov. 14, 2019

(65) Prior Publication Data

US 2021/0150703 A1    May 20, 2021

(51) Int. Cl.
*G06N 3/04* (2023.01)
*G16H 30/40* (2018.01)
*G06T 7/00* (2017.01)
*G06N 3/08* (2023.01)
*G16H 30/20* (2018.01)
*G06F 18/24* (2023.01)
*G06V 10/764* (2022.01)
*G06V 10/82* (2022.01)

(52) U.S. Cl.
CPC ............. *G16H 30/40* (2018.01); *G06F 18/24* (2023.01); *G06N 3/04* (2013.01); *G06N 3/08* (2013.01); *G06T 7/0012* (2013.01); *G06V 10/764* (2022.01); *G06V 10/82* (2022.01); *G16H 30/20* (2018.01); *G06T 2207/20081* (2013.01); *G06T 2207/20084* (2013.01); *G06T 2207/30068* (2013.01)

(58) Field of Classification Search
None
See application file for complete search history.

(56) References Cited

U.S. PATENT DOCUMENTS

| 9,466,012 | B2* | 10/2016 | Ritt ....................... G06F 18/285 |
| 9,589,374 | B1* | 3/2017 | Gao ....................... A61B 6/5211 |
| 10,872,292 | B1* | 12/2020 | Yang ..................... G06T 5/20 |
| 11,282,535 | B2* | 3/2022 | Choo ..................... G10L 25/30 |
| 2011/0255741 | A1* | 10/2011 | Jung ..................... G06V 20/58 382/103 |
| 2015/0016699 | A1* | 1/2015 | Ritt ....................... G06F 18/217 382/128 |
| 2016/0259994 | A1 | 12/2016 | Ravindran et al. |
| 2019/0183429 | A1* | 6/2019 | Sung ..................... A61B 5/7267 |
| 2020/0043600 | A1* | 2/2020 | Glottmann ............. G16H 15/00 |

(Continued)

FOREIGN PATENT DOCUMENTS

CN    109741317 A    5/2019

OTHER PUBLICATIONS

Razzak, Muhammad Imran et al., "Deep Learning for Medical Image Processing: Overview, Challenges and Future," Dey N., Ashour A., Borra S. (eds) Classification in BioApps. Lecture Notes in Computational Vision and Biomechanics, vol. 26. Springer, Cham. pp. 30.

*Primary Examiner* — Tsung Yin Tsai
(74) *Attorney, Agent, or Firm* — Barry D. Blount

(57) ABSTRACT

An example system includes a processor to receive an image with corresponding acquisition information. The processor is to classify the image using the corresponding acquisition information via a deep neural network including integrated acquisition information.

20 Claims, 7 Drawing Sheets

(56) References Cited

U.S. PATENT DOCUMENTS

2020/0160966 A1\* 5/2020 Lyman .................. G06T 11/206
2020/0342893 A1\* 10/2020 Choo ....................... G10L 25/30
2021/0073613 A1\* 3/2021 Yang ......................... G06T 5/20

\* cited by examiner

100

200

CLASSIFYING IMAGES USING DEEP NEURAL NETWORK WITH INTEGRATED ACQUISITION INFORMATION

BACKGROUND

The present techniques relate to classification of images. More specifically, the techniques relate to classification of medical images.

SUMMARY

According to an embodiment described herein, a system can include processor to receive an image with corresponding acquisition information. The processor can also further classify the image using the corresponding acquisition information via a deep neural network including integrated acquisition information.

According to another embodiment described herein, a computer-implemented method can include receiving, at a trained deep neural network including integrated acquisition information, an image with corresponding acquisition information. The method can further include classifying, via the trained deep neural network, the image using the corresponding acquisition information.

According to another embodiment described herein, a computer program product for classifying images can include computer-readable storage medium having program code embodied therewith. The computer readable storage medium is not a transitory signal per se. The program code executable by a processor to cause the processor to receive an image with corresponding acquisition information at a trained deep neural network including integrated acquisition information. The program code can also cause the processor to classify the image using the corresponding acquisition information.

DETAILED DESCRIPTION

Figure 1:
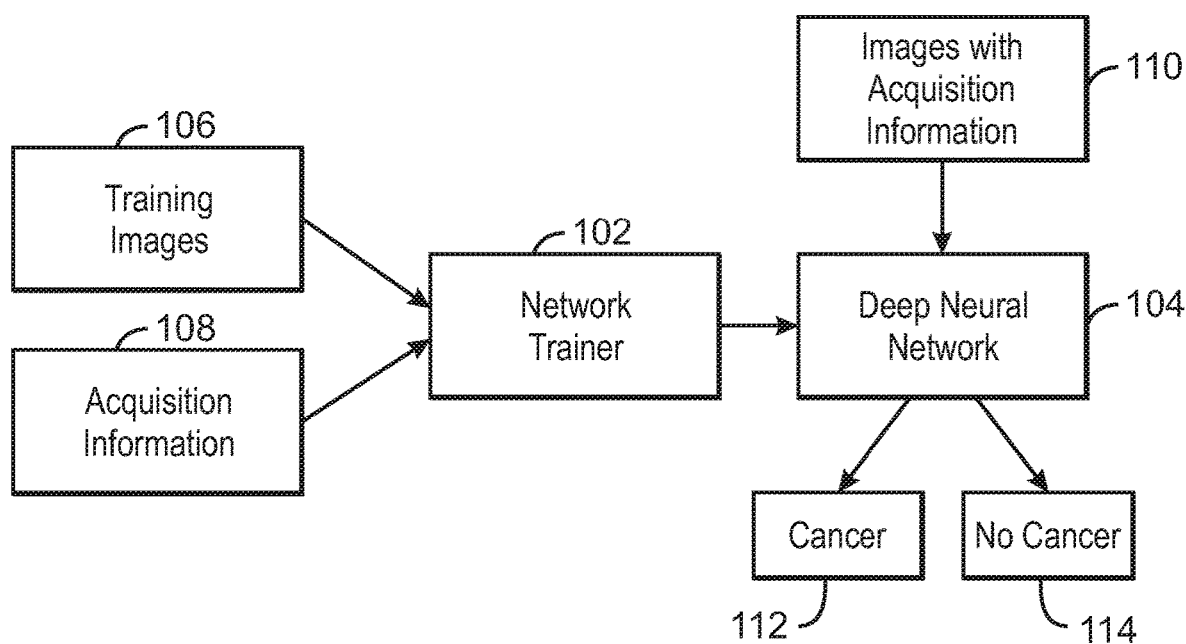
FIG. 1 is a block diagram of an example system for classification of images using integrated acquisition information.

Images taken using mammography pose significant challenges with regards to detection of cancer in the images. In particular, mammography images are sensitive to both patient related issues and to acquisition related factors. For example, patient related issues may include differences in breast density and breast size, among other factors.

Acquisition information related to images taken using mammography includes machine parameters. For example, the parameters may include the model or the image software installed on a specific model of a mammography machine. As one example, Digital Imaging and Communications in Medicine (DICOM®) is the standard for the communication and management of medical imaging information and related data. DICOM® is used for storing and transmitting medical images enabling the integration of medical imaging devices such as scanners, servers, workstations, printers, network hardware, and picture archiving and communication systems (PACS) from multiple manufacturers. DICOM® files can be exchanged between two entities that are capable of receiving image and patient data in DICOM® format. Different devices may come with DICOM® Conformance Statements which clearly state which DICOM® classes they support, and the standard includes a file format definition and a network communications protocol that uses Transmission Control Protocol/Internet Protocol (TCP/IP) to communicate between systems. The DICOM® information object definitions encode the data produced by a wide variety of imaging device types, including, CT (computed tomography), MRI (magnetic resonance imaging), ultrasound, X-ray, fluoroscopy, angiography, mammography, breast tomosynthesis, PET (positron emission tomography), SPECT (single photon emission computed tomography), Endoscopy, microscopy, nd whole slide imaging, and OCT (optical coherence tomography), among other devices. DICOM® is also implemented by devices associated with images or imaging workflow including, PACS (picture archiving and communication systems), image viewers and display stations, CAD (computer-aided detection/diagnosis systems), 3D visualization systems, clinical analysis applications, image printers, Film scanners, media burners (that export DICOM® files onto CDs, DVDs, etc.), media importers (that import DICOM® files from CDs, DVDs, USBs, etc.), RIS (radiology information systems), VNA (vendor-neutral archives), EMR (electronic medical record) systems, and radiology reporting systems.

According to embodiments of the present disclosure, a processor can classify images using integrated acquisition information. For example, a processor may receive an image with corresponding acquisition information. A deep neural network having integrated acquisition information may classify the image using the corresponding acquisition information. In various examples, the integrated acquisition information may be a mask that is applied to one or more layers of the deep neural network. In some examples, the integrated acquisition information may be concatenated to a feature before a decision layer of the deep neural network. Thus, embodiments of the present disclosure allow improved accuracy in classification of medical images. For example, the embodiments may be used to more accurately classify mammography images as cancerous or benign.

With reference now to FIG. 1, a block diagram shows an example system for classification of images using integrated acquisition information. The example system is generally referred to by the reference number 100. FIG. 1 includes a network trainer 102 communicatively coupled to a deep neural network (DNN) 104. For example, the deep neural network may be a convolutional neural network 104. The network trainer 102 is shown receiving training images 106 and acquisition information 108. For example, the training images 106 and acquisition information 108 may be received in the form of DICOM® data used for training, and extracted therefrom. The deep neural network 104 is shown receiving images with corresponding acquisition information 110. For example, the images with acquisition information 110 may be medical images, such as mammography scans, with acquisition information corresponding to particular patients. The deep neural network 104 is shown classifying the images 110 as including cancer 112 or not including cancer 114.

In the example of FIG. 1, a deep neural network 104 may be trained by a network trainer 102 to integrate acquisition information for classifying images. For example, the network trainer 102 may use acquisition information related to acquisition of the images to train the deep neural network 104. As one example, the acquisition information may include one or more fields from the DICOM® data, including "KVP", "CompressionForce", "BodyPartThickness", "DistanceSourceToDetector", "Exposure", "ExposureTime", "OrganDose", "RelativeXRayExposure", "XRayTubeCurrent", etc.

Still referring to FIG. 1, the acquisition information may be integrated into the deep neural network 104 to produce an analysis of the image. For example, the network trainer 102 can learn a mask that integrates the acquisition information. For example, the processor can learn the mask by operating a number of fully connected layers. In various examples, the network trainer 102 learns the mask individually for each layer of the deep neural network. The network trainer 102 can then apply the learned mask to a deep neural network. For example, the network trainer 102 can apply the learned mask to different convolutional layers at different depths of the deep neural network. In various examples, the network trainer 102 can apply the same mask to one or more layers of the deep neural network. In some examples, the network trainer 102 can concatenate the mask to a feature before a decision layer of the deep neural network.

The trained DNN 104 with the mask that integrates the acquisition information may then output classifications given an input image and associated acquisition information. In some examples, the DNN 104 may also output analysis of the image. For example, the analysis may include a cancer detection, a breast density, or risk, among other analyses.

It is to be understood that the block diagram of FIG. 1 is not intended to indicate that the system 100 is to include all of the components shown in FIG. 1. Rather, the system 100 can include fewer or additional components not illustrated in FIG. 1 (e.g., additional neural networks, or additional training images, images with acquisition information, classifications, network trainers, etc.).

Figure 2:
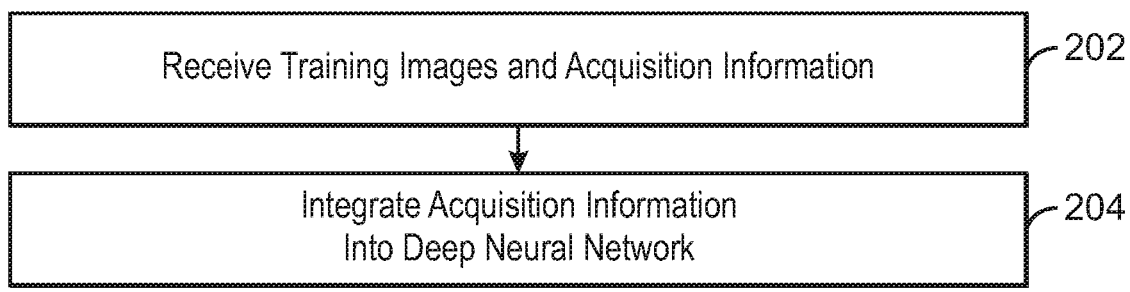
FIG. 2 is a block diagram of an example method that can classify images using integrated acquisition information.

FIG. 2 is a process flow diagram of an example method that can train a deep neural network to classify images using integrated acquisition information. The method 200 can be implemented with any suitable computing device, such as the computing device 400 of FIG. 4 and is described with reference to the system 100 of FIG. 1. For example, the methods described below can be implemented by the processor 402 or the processor 702 of FIGS. 4 and 7.

At block 202, a processor receives training images with corresponding acquisition information. For example, the acquisition information may include information about how the training images were acquired.

At block 204, the processor integrates the acquisition information into a deep neural network. For example, the processor can learn a mask by operating a number of fully connected layers and apply the learned mask to different convolutional layers at different depths of the deep neural network. In various examples, the processor learns the mask individually for each layer of the deep neural network. In some examples, the processor concatenates the acquisition information to a feature before a decision layer of the deep neural network. In various examples, the processor concatenates the acquisition information with one or more layers in the deep neural network.

The process flow diagram of FIG. 2 is not intended to indicate that the operations of the method 200 are to be executed in any particular order, or that all of the operations of the method 200 are to be included in every case. Additionally, the method 200 can include any suitable number of additional operations.

Figure 3:
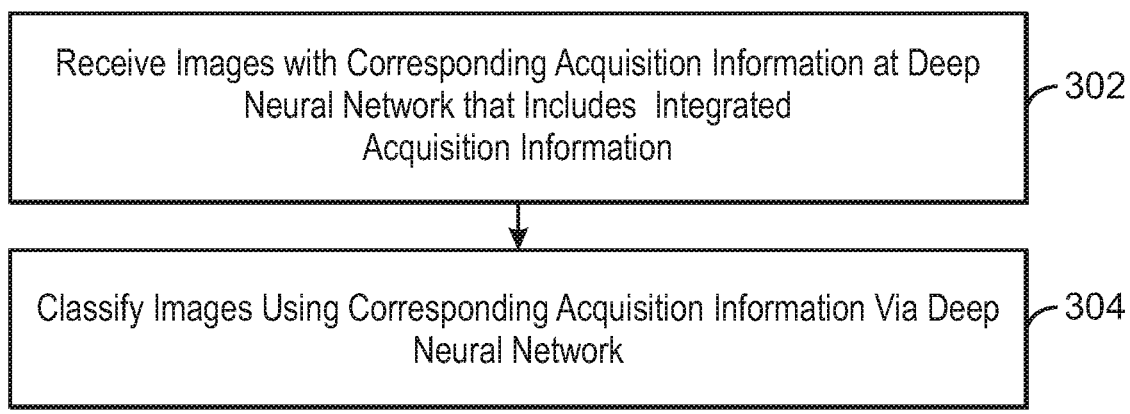
FIG. 3 is a block diagram of an example method that can train a deep neural network to classify images using integrated acquisition information.

FIG. 3 is a process flow diagram of an example method that can classify images using integrated acquisition information. The method 300 can be implemented with any suitable computing device, such as the computing device 400 of FIG. 4 and is described with reference to the system 100 of FIG. 1. For example, the methods described below can be implemented by the processor 402 or the processor 702 of FIGS. 4 and 7.

At block 302, a trained deep neural network that includes integrated acquisition information receives an image with corresponding acquisition information. For example, the corresponding acquisition information may include information about how the image was captured.

At block 304, the trained deep neural network classifies the image using the corresponding acquisition information. For example, the trained deep neural network may classify the image as a cancer. In some examples, the trained deep neural network may also generate a breast density. For example, breast density may be included as a risk factor for cancer. In various examples, the trained deep neural network may generate a risk. For example, the risk may represent the chance of having cancer, or the chance of developing cancer in the future.

The process flow diagram of FIG. 3 is not intended to indicate that the operations of the method 300 are to be executed in any particular order, or that all of the operations of the method 300 are to be included in every case. Additionally, the method 300 can include any suitable number of additional operations.

In some scenarios, the techniques described herein may be implemented in a cloud computing environment. As discussed in more detail below in reference to at least FIGS. 4-7, a computing device configured to classify images using a deep neural network with integrated acquisition information may be implemented in a cloud computing environment. It is understood in advance that although this disclosure may include a description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
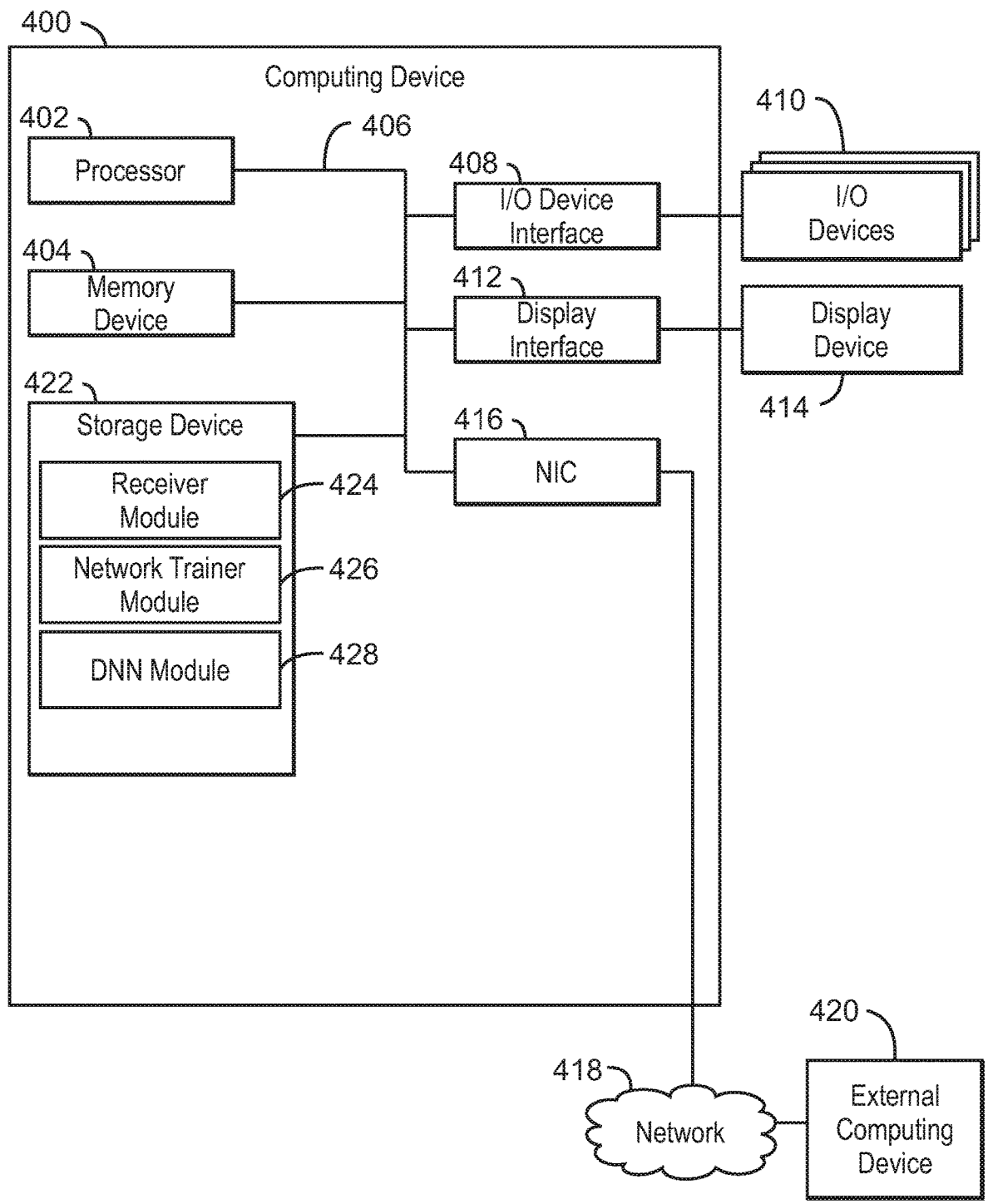
FIG. 4 is a block diagram of an example computing device that can classify images using integrated acquisition information.

FIG. 4 is block diagram of an example computing device that can classify images using integrated acquisition information. The computing device 400 may be for example, a server, desktop computer, laptop computer, tablet computer, or smartphone. In some examples, computing device 400 may be a cloud computing node. Computing device 400 may be described in the general context of computer system executable instructions, such as program modules, being executed by a computer system. Generally, program modules may include routines, programs, objects, components, logic, data structures, and so on that perform particular tasks or implement particular abstract data types. Computing device 400 may be practiced in distributed cloud computing environments where tasks are performed by remote processing devices that are linked through a communications network. In a distributed cloud computing environment, program modules may be located in both local and remote computer system storage media including memory storage devices.

The computing device 400 may include a processor 402 that is to execute stored instructions, a memory device 404 to provide temporary memory space for operations of said instructions during operation. The processor can be a single-core processor, multi-core processor, computing cluster, or any number of other configurations. The memory 404 can include random access memory (RAM), read only memory, flash memory, or any other suitable memory systems.

The processor 402 may be connected through a system interconnect 406 (e.g., PCI®, PCI-Express®, etc.) to an input/output (I/O) device interface 408 adapted to connect the computing device 400 to one or more I/O devices 410. The I/O devices 410 may include, for example, a keyboard and a pointing device, wherein the pointing device may include a touchpad or a touchscreen, among others. The I/O devices 410 may be built-in components of the computing device 400, or may be devices that are externally connected to the computing device 400.

The processor 402 may also be linked through the system interconnect 406 to a display interface 412 adapted to connect the computing device 400 to a display device 414. The display device 414 may include a display screen that is a built-in component of the computing device 400. The display device 414 may also include a computer monitor, television, or projector, among others, that is externally connected to the computing device 400. In addition, a network interface controller (NIC) 416 may be adapted to connect the computing device 400 through the system interconnect 406 to the network 418. In some embodiments, the NIC 416 can transmit data using any suitable interface or protocol, such as the internet small computer system interface, among others. The network 418 may be a cellular network, a radio network, a wide area network (WAN), a local area network (LAN), or the Internet, among others. An external computing device 420 may connect to the computing device 400 through the network 418. In some examples, external computing device 420 may be an external web-server 420. In some examples, external computing device 420 may be a cloud computing node.

The processor 402 may also be linked through the system interconnect 406 to a storage device 422 that can include a hard drive, an optical drive, a USB flash drive, an array of drives, or any combinations thereof. In some examples, the storage device may include a receiver module 424, a network trainer module 426, and a deep neural network (DNN) module 428. The receiver module 424 can receive an image with corresponding acquisition information. For example, the acquisition information may include information related to an acquisition process of the image. In some examples, the acquisition information and image is received as Digital Imaging and Communications in Medicine (DICOM®) data. The network trainer module 426 can train a DNN to integrate acquisition information into the DNN. For example, the network trainer module 426 can learn a mask that integrated the acquisition information by operating a number of fully connected layers and apply the learned mask to different convolutional layers in different depths of the deep neural network. In some examples, the network trainer module 426 can learn the mask individually for each layer of the deep neural network. In various examples, the network trainer module 426 can concatenate the integrated acquisition information to a feature before a decision layer of the deep neural network. The DNN module 428 can classify the image using the corresponding acquisition information via a deep neural network including the integrated acquisition information. In various examples, the classification of the image may include a cancer detection, a breast density, a risk, or any combination thereof.

It is to be understood that the block diagram of FIG. 4 is not intended to indicate that the computing device 400 is to include all of the components shown in FIG. 4. Rather, the computing device 400 can include fewer or additional components not illustrated in FIG. 4 (e.g., additional memory components, embedded controllers, modules, additional network interfaces, etc.). Furthermore, any of the functionalities of the receiver module 424, the network trainer module 426, and the DNN module 428 may be partially, or entirely, implemented in hardware and/or in the processor 402. For example, the functionality may be implemented with an application specific integrated circuit, logic implemented in an embedded controller, or in logic implemented in the processor 402, among others. In some embodiments, the functionalities of the receiver module 424, the network trainer module 426, and the DNN module 428 can be implemented with logic, wherein the logic, as referred to herein, can include any suitable hardware (e.g., a processor, among others), software (e.g., an application, among others), firmware, or any suitable combination of hardware, software, and firmware.

Figure 5:
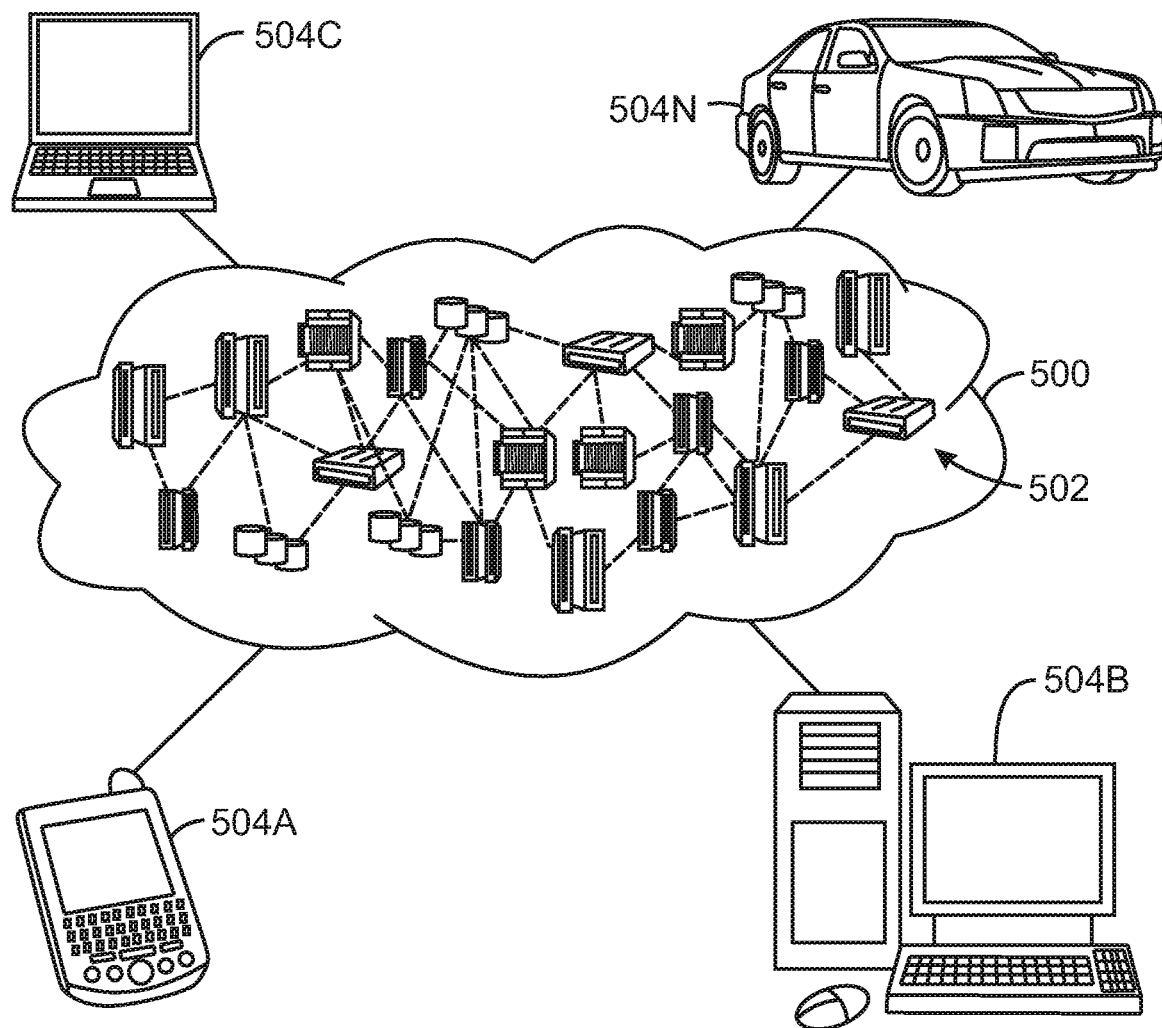
FIG. 5 is a diagram of an example cloud computing environment according to embodiments described herein.

Referring now to FIG. 5, illustrative cloud computing environment 500 is depicted. As shown, cloud computing environment 500 comprises one or more cloud computing nodes 502 with which local computing devices used by cloud consumers, such as, for example, personal digital assistant (PDA) or cellular telephone 504A, desktop computer 504B, laptop computer 504C, and/or automobile computer system 504N may communicate. Nodes 502 may communicate with one another. They may be grouped (not shown) physically or virtually, in one or more networks, such as Private, Community, Public, or Hybrid clouds as described hereinabove, or a combination thereof. This allows cloud computing environment 500 to offer infrastructure, platforms and/or software as services for which a cloud consumer does not need to maintain resources on a local computing device. It is understood that the types of computing devices 504A-N shown in FIG. 5 are intended to be illustrative only and that computing nodes 502 and cloud computing environment 500 can communicate with any type of computerized device over any type of network and/or network addressable connection (e.g., using a web browser).

Figure 6:
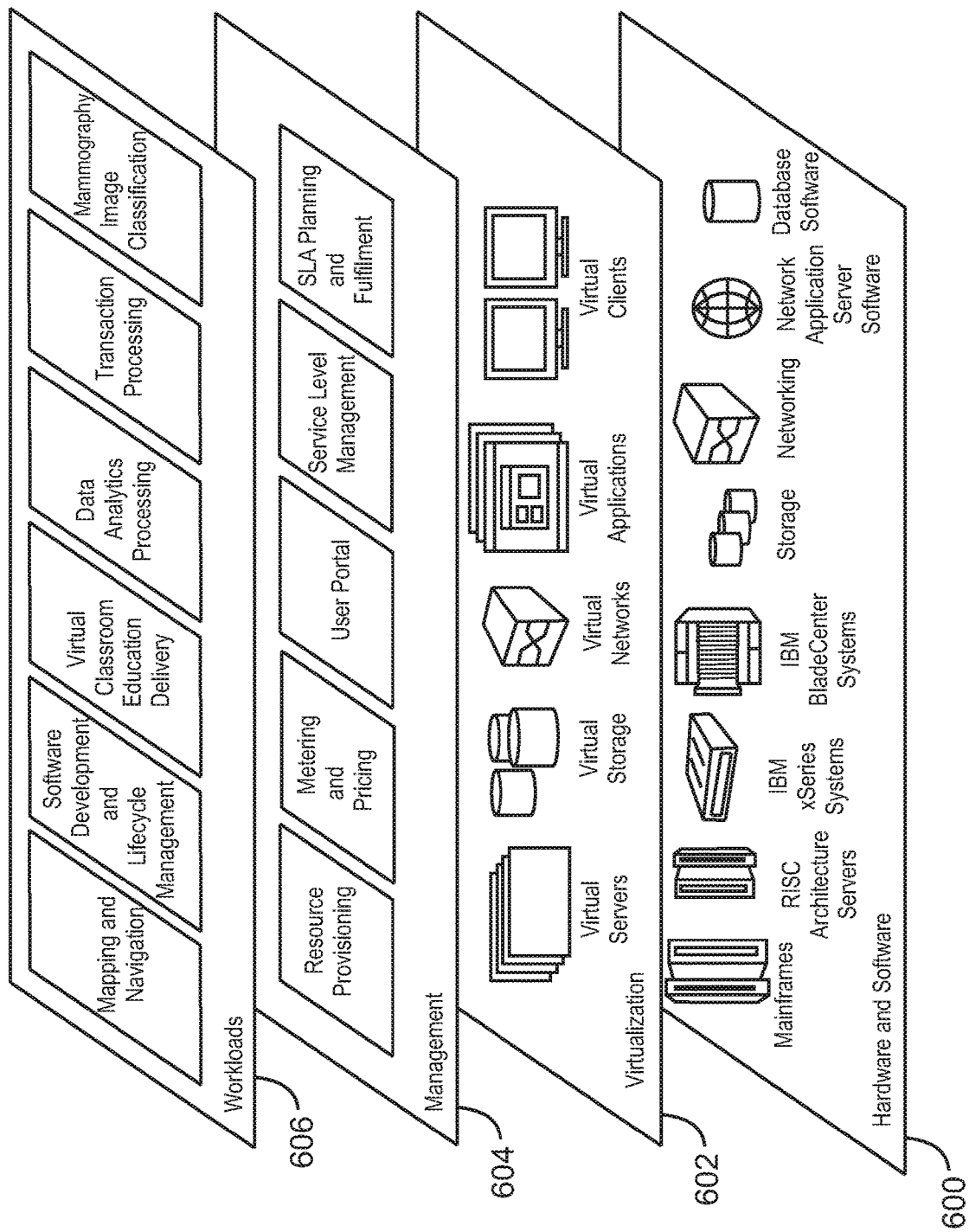
FIG. 6 is a diagram of an example abstraction model layers according to embodiments described herein.

Referring now to FIG. 6, a set of functional abstraction layers provided by cloud computing environment 500 (FIG. 5) is shown. It should be understood in advance that the components, layers, and functions shown in FIG. 6 are intended to be illustrative only and embodiments of the invention are not limited thereto. As depicted, the following layers and corresponding functions are provided.

Hardware and software layer 600 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 602 provides an abstraction layer from which the following examples of virtual entities may be provided: virtual servers; virtual storage; virtual networks, including virtual private networks; virtual applications and operating systems; and virtual clients. In one example, management layer 604 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 606 provides examples of functionality for which the cloud computing environment may be utilized. Examples of workloads and functions which may be provided from this layer include: mapping and navigation; software development and lifecycle management; virtual classroom education delivery; data analytics processing; transaction processing; and mammography image classification.

The present invention may be a system, a method and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the techniques. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 7:
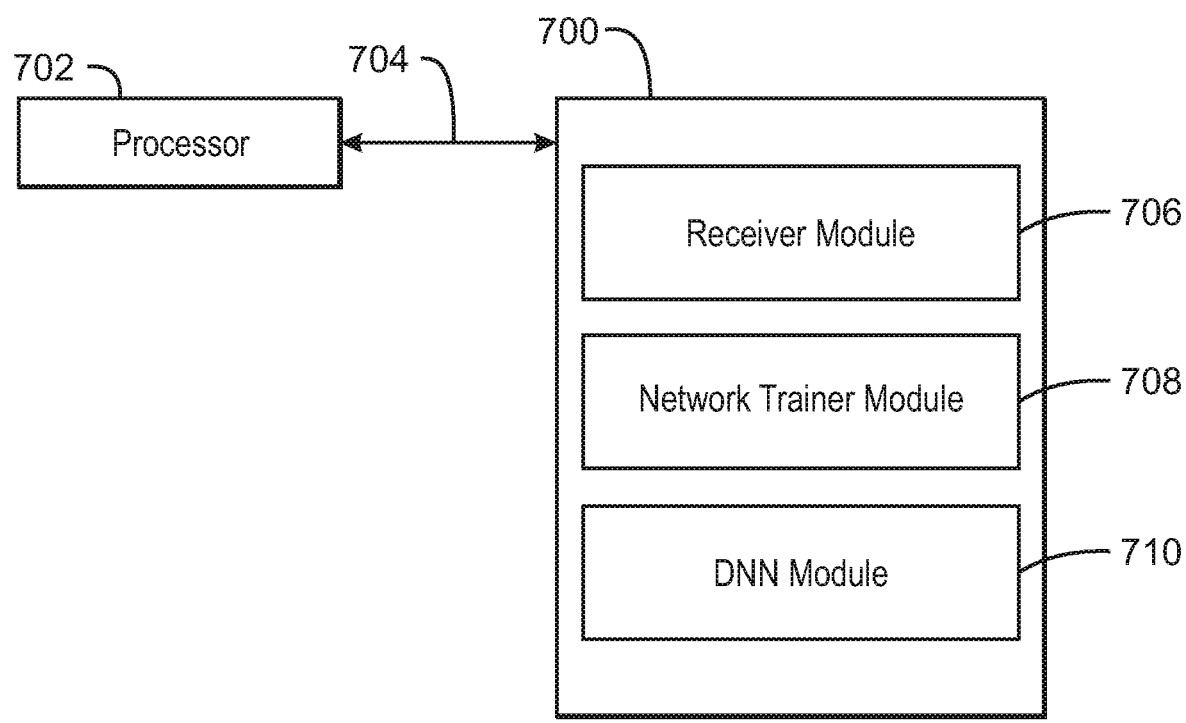
FIG. 7 is an example tangible, non-transitory computer-readable medium that can classify images using integrated acquisition information.

Referring now to FIG. 7, a block diagram is depicted of an example tangible, non-transitory computer-readable medium 700 that can classify images using integrated acquisition information. The tangible, non-transitory, computer-readable medium 700 may be accessed by a processor 702 over a computer interconnect 704. Furthermore, the tangible, non-transitory, computer-readable medium 700 may include code to direct the processor 702 to perform the operations of the methods 200 and 300 of FIGS. 2 and 3.

The various software components discussed herein may be stored on the tangible, non-transitory, computer-readable medium 700, as indicated in FIG. 7. For example, a receiver module 706 includes code to receive an image with corresponding acquisition information at a trained deep neural network including integrated acquisition information. A network trainer module 708 includes code to train a deep neural network to integrate acquisition information into the deep neural network. For example, the network trainer module 708 may include code to operate a number of fully connected layers to learn a mask that integrated acquisition information and apply the learned mask to different convolutional layers at different depths of the deep neural network. The network trainer module 708 also includes code to concatenate the integrated acquisition information to a feature before a decision layer of the deep neural network. In some examples, the network trainer module 708 also includes code to learn a mask individually for each layer of the deep neural network to integrate the acquisition information. The deep neural network (DNN) module 710 includes code to receive an image with corresponding acquisition information. For example, the DNN module 710 may include a trained DNN including integrated acquisition information. The DNN module 710 also includes code to classify the image using the corresponding acquisition information. For example, the DNN module 710 may include code to classify the image as cancerous. In some examples, the DNN module 710 may include code to generate a breast density, a risk, or both. It is to be understood that any number of additional software components not shown in FIG. 7 may be included within the tangible, non-transitory, computer-readable medium 700, depending on the particular application.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. It is to be understood that any number of additional software components not shown in FIG. 7 may be included within the tangible, non-transitory, computer-readable medium 700, depending on the specific application.

The descriptions of the various embodiments of the present techniques have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising a processor to:
receive an image with corresponding acquisition information; and
classify the image using the corresponding acquisition information as input into a deep neural network that comprises a learned mask, wherein the learned mask is learned by operating a fully connected layer in the deep neural network and the same mask is then applied to a plurality of layers of the deep neural network to integrate acquisition information into the deep neural network.

2. The system of claim 1, wherein the integrated acquisition information comprises the learned mask that is learned by operating a plurality of fully connected layers and applied to different convolutional layers in different depths of the deep neural network.

3. The system of claim 1, wherein the integrated acquisition information comprises the learned mask that is learned individually for each layer of the deep neural network.

4. The system of claim 1, wherein the learned mask that integrates the acquisition information is concatenated to a feature before a decision layer of the deep neural network.

5. The system of claim 1, wherein the classification of the image comprises a cancer detection, a breast density, a risk, or any combination thereof.

6. The system of claim 1, wherein the acquisition information comprises information related to an acquisition process of the image.

7. The system of claim 1, wherein the acquisition information and image is received as Digital Imaging and Communications in Medicine (DICOM®) data.

8. A computer-implemented method, comprising:
receiving, at a trained deep neural network comprising integrated acquisition information, an image with corresponding acquisition information; and
classifying, via the trained deep neural network, the image using the corresponding acquisition information as input into a deep neural network that comprises a learned mask, wherein the learned mask is learned by operating a fully connected layer in the deep neural network and the same mask is then applied to a plurality of layers of the deep neural network to integrate acquisition information into the deep neural network.

9. The computer-implemented method of claim 8, comprising learning the learned mask by operating a plurality of fully connected layers and applying the learned mask to different convolutional layers at different depths of the deep neural network to integrate the acquisition information into the trained deep neural network.

10. The computer-implemented method of claim 8, comprising training the deep neural network by concatenating the learned mask to a feature before a decision layer of the deep neural network.

11. The computer-implemented method of claim 8, comprising learning the learned mask individually for each layer of the deep neural network to integrate the acquisition information into the trained deep neural network.

12. The computer-implemented method of claim 8, wherein classifying the image comprises generating comprises classifying the images as a cancer.

13. The computer-implemented method of claim 8, wherein classifying the image comprises generating comprises generating a breast density.

14. The computer-implemented method of claim 8, wherein classifying the image comprises generating comprises generating a risk.

15. A computer program product for classifying images, the computer program product comprising a computer-readable storage medium having program code embodied therewith, the program code executable by a processor to cause the processor to:
receive an image with corresponding acquisition information at a trained deep neural network comprising integrated acquisition information; and
classify the image using the corresponding acquisition information as input into a deep neural network that comprises a learned mask, wherein the learned mask is learned by operating a fully connected layer in the deep neural network and the same mask is then applied to a plurality of layers of the deep neural network to integrate acquisition information into the deep neural network.

16. The computer program product of claim 15, further comprising program code executable by the processor to operate a plurality of fully connected layers to learn the learned mask that integrates the acquisition information and apply the learned mask to different convolutional layers at different depths of the deep neural network.

17. The computer program product of claim 15, further comprising program code executable by the processor to concatenate the integrated acquisition information to a feature before a decision layer of the deep neural network.

18. The computer program product of claim 15, further comprising program code executable by the processor to learn the learned mask individually for each layer of the deep neural network to integrate the acquisition information.

19. The computer program product of claim 15, further comprising program code executable by the processor to classify the image as cancerous.

20. The computer program product of claim 15, further comprising program code executable by the processor to generate a breast density.

\* \* \* \* \*